United States Patent [19]

Tamao et al.

[11] Patent Number: 5,498,736
[45] Date of Patent: Mar. 12, 1996

[54] 2,5-REACTIVE SUBSTITUENT GROUP-CONTAINING SILOLES, SILOLE POLYCONDENSATES AND PREPARATION THEREOF

[75] Inventors: Kohei Tamao, Kyoto; Shigehiro Yamaguchi, Uji, both of Japan

[73] Assignee: Shin-Etsu Chemical Co., Ltd., Tokyo, Japan

[21] Appl. No.: 360,006

[22] Filed: Dec. 20, 1994

[30] Foreign Application Priority Data

Dec. 21, 1993 [JP] Japan .................................. 5-345214
Mar. 11, 1994 [JP] Japan .................................. 6-067988

[51] Int. Cl.$^6$ .................................................. C07F 7/08
[52] U.S. Cl. ........................... 556/406; 556/11; 556/12; 556/404
[58] Field of Search ............................ 556/406, 404, 556/11, 12

[56] References Cited

U.S. PATENT DOCUMENTS 3,151,140  9/1964  Hubel et al. ............................ 556/406
3,426,052  2/1969  Hubel et al. ............................ 556/9

Primary Examiner—Paul F. Shaver
Attorney, Agent, or Firm—Birch, Stewart, Kolasch & Birch

[57] ABSTRACT

2,5-Reactive substituent group-containing siloles of the following general formula are provided

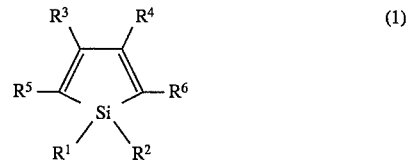

wherein $R^1$ to $R^4$ may be the same or different and independently represent a monovalent hydrocarbon group having from 1 to 12 carbon atoms or a hydrogen atom, and $R^5$ and $R^6$ may be the same or different and independently represent a group selected from monovalent hydrocarbon-substituted sulfur, selenium, silicon, germanium, tin and phosphorus, or a halogen atom. Polycondensates of the siloles and processes for preparing the siloles and polycondensates are described.

31 Claims, 1 Drawing Sheet

FIG.1

2,5-REACTIVE SUBSTITUENT GROUP-CONTAINING SILOLES, SILOLE POLYCONDENSATES AND PREPARATION THEREOF

BACKGROUND OF THE INVENTION

1. Field of the Invention

This invention relates to 2,5-reactive substituent group-containing siloles which are novel π-electron conjugated organic compounds having a light absorption band or bands in the range of UV to visible light, and also to polycondensates and intermediates thereof. The invention also relates to processes for preparing such siloles, polycondensates and intermediates as set out above.

2. Description of the Prior Art

Highly stable polymers such as polyacetylene, polythiophene, polypyrrole and the like have been hitherto reported as π-electron conjugated organic polymers and their development for use as organic conductive materials has been studied. In recent years, aside from the homopolymers, there have been prepared various copolymers such as of combinations of thiophene and pyrrole. Attention has been drawn to these materials, with the possibility that they are applicable as a new functional material in view of their unique light absorption spectra ascribed to the intramolecular donative and acceptive structure of electrons.

On the other hand, polymerization of siloles has been studied because the silole skeleton has a structure serving as both an electron donor and an electron acceptor. We have already proposed in Japanese Patent Application Nos. 4-196609 and 5-82620 copolymers having both a silole structure and a thiophene structure, with the expectation that such polymers can be applied as an optical functional material owing to the very unique light absorption characteristics thereof. In this connection, Barton et al has shown that according to the theoretical calculation, the polysilole bonded at the 2,5 positions has a possibility of providing a polymer whose non-linear optical characteristics are good. Moreover, Frapper et al reported that such a polysilole as mentioned above has so small a band gap that there is a high possibility for use as a conductive material. However, hitherto known processes involve a difficulty in introducing reactive groups into silole compounds at the 2,5 positions. Satisfactory studies have never been made on the preparation of 2,5-reactive substituent-containing siloles up to now, with the exception that Wrackmeyer et al (Chem. Comm., 86, 397) reported the preparation of siloles having a boron substituent at the 3 position and two stannyl substituents at the 2,5 positions by reaction between bis(2-stannylethynyl)silane and boranes.

SUMMARY OF THE INVENTION

An object of the invention is to provide 2,5-reactive substituent group-containing siloles, silole polycondensates and intermediates thereof, and also processes for preparing the same.

As a result of intensive studies for achieving the above object, we found that a silane compound of the following general formula (3) is reacted with an alkali metal or an alkali metal complex (M) to obtain an intermediate of the following general formula (2), and the intermediate is further reacted with $R^5X$ and $R^6X$ to obtain a 2,5-reactive substituent-containing silole of the following general formula (1) having at the 2,5 positions a group selected from sulfur, selenium, silicon, germanium, tin and phosphorus substituted with a monovalent hydrocarbon, or a halogen atom wherein $R^1$ to $R^4$ may be the same or different and independently represent a monovalent hydrocarbon group having from 1 to 12 carbon atoms or a hydrogen atom, $R^5$ and $R^6$ may be the same or different and independently represent a group selected from sulfur, selenium, silicon, germanium, tin and phosphorus each substituted with a monovalent hydrocarbon group, or a halogen atom, M represents an alkali metal or an alkali metal complex, and X represents a halogen atom provided that $R^5X$ and $R^6X$ may be the same or different.

It has also been found that the 2,5-reactive substituent-containing silole is useful as a starting material for optical functional materials such as conductive organic materials, non-linear optical materials, photoresponse materials or as a starting material for copolymerization with other π-electron conjugated polymers or the monomers thereof in order to obtain such optical functional materials as mentioned above.

We have also found that a dihalogenosilole of the following general formula (6) is reacted with an alkylated product of an alkali metal to obtain a 2,5-reactive substituent-containing silole of the formula (4) and that when the silole of the formula (4) is subjected to polycondensation under oxidative conditions in the presence of a cuprous compound or when a silole polycondensate of the formula (7) obtained from the silole of the formula (4) is subjected to further polycondensation in a manner similar to the above, there is obtained a silole polycondensate of the formula (5) is obtained.

wherein $R^1$ to $R^4$, X and M have, respectively, the same meanings as defined hereinbefore, A and B may be the same or different and independently represent a hydrogen atom, a halogen atom or an alkali metal atom, n is an integer of 2 or over, m is an integer of 1 or over provided that n>m.

Further, it has been found that a reactive halogen-containing compound is acted on the dialkali silole of the following formula (8), followed by condensation in the presence of an iron (III) acetylacetonate to obtain a silole polycondensate of the following formula (9)

wherein $R^1$ and $R^4$ and M have, respectively, the same meanings as defined before, p is an integer of 2 or over.

It has also been found that a compound of the formula, AX, wherein A represents sulfur, selenium, silicon, germanium, tin or phosphorus each having monovalent hydrocarbon substituents, and X represents a halogen atom, is reacted with the silole of the formula (4), thereby obtaining a 2,5-different reactive substituent group-containing silole compound of the following formula (10) and that the silole compound of the formula (10) is polycondensed in the presence of a catalyst such as palladium and palladium compounds to obtain the silole polycondensate wherein $R^1$ to $R^4$, A and X have, respectively, the same meanings as defined before.

The silole polycondensates obtained herein are useful as optical functional materials such as conductive organic materials, non-linear optical materials, photoresponse materials and the like, or as a starting material for copolymerization with other π-conjugated polymers or monomers thereof in order to obtain the optical functional materials. The invention has been accomplished based on these findings.

Thus, the invention provides a 2,5-reactive substituent group-containing silole of the formula (1), a 2,5-reactive substituent group-containing silole of the formula (2) which is an intermediate of the compound of the formula (1), a process for preparing the silole of the formula (1) by reaction between the silole (2) and $R^5X$ and $R^6X$, and a process for preparing the silole of the formula (2) by reaction between the silane compound of the formula (3) and an alkali metal or an alkali metal complex. Also, the invention provides a process for preparing a silole of the formula (1) by reaction between a silane compound of the formula (3) and an alkali metal or an alkali metal complex and further reaction between the resultant mixture and $R^5X$ and $R^6X$.

Further embodiments of the invention include a 2,5-reactive substituent group-containing silole of the formula (4), a silole polycondensate of the formula (5), and a process for preparing a 2,5-reactive substituent group-containing silole of the formula (4) by reaction between the dihalogenosilole of the formula (6) and an alkylated product of an alkali metal. Still further embodiments include a process for preparing a silole polycondensate of the formula (5) by polycondensation of a silole of the formula (7) and a silole polycondensate under oxidative conditions in the presence of a cuprous compound, a process for preparing a silole polycondensate wherein a reactive halogen compound is reacted with a dialkali silole of the formula (8), followed by condensation in the presence of a catalyst of iron (III) acetylacetonate, a 2,5-different reactive substituent groups-containing silole of the formula (10), and a process for preparing the silole of the formula (10) by reaction of a silole of the formula (4) with a compound of the formula, AX, defined hereinbefore.

DETAILED DESCRIPTION OF THE INVENTION

The 2,5-reactive substituent group-containing silole of the invention is of the following general formula (1)

wherein $R^1$ to $R^4$ may be the same or different and independently represent a hydrogen atom or a monovalent hydrocarbon group having from 1 to 12 carbon atoms, and $R^5$ and $R^5$ may be the same or different and independently represent a group selected from sulfur, selenium, silicon, germanium, tin and phosphorus each substituted with a monovalent hydrocarbon, or a halogen atom.

$R^1$ to $R^4$ are as set out above and preferably, the monovalent hydrocarbon group represented by $R^1$ to $R^4$ includes an alkyl group having from 1 to 10 carbon atoms, an aryl group having from 6 to 10 carbon atoms, and an aralkyl group having from 7 to 12 carbon atoms. Specific examples include an alkyl group such as methyl, ethyl, propyl, cyclohexyl or the like, an aryl group such as phenyl, tolyl, xylyl or the like, and an aralkyl group such as benzyl, phenethyl or the like. In this case, $R^3$ and $R^4$ should more preferably be an aryl group having from 6 to 10 carbon atoms.

$R^5$ and $R^6$ are, respectively, those defined above. Specific examples include substituted silyl groups represented by the formula, $R^7R^8R^9Si$, e.g. trimethylsilyl group, tributylsilyl group, phenyldimethylsilyl group and the like, substituted germyl groups represented by the formula, $R^7R^8R^9Ge$, e.g. trimethylgermyl group, substituted stannyl groups represented by the formula, $R^7R^8R^9Sn$, e.g. trimethylstannyl group, tributylstannyl group, phenyldimethylstannyl group and the like, substituted selenyl groups represented by the formula, $R^7Se$, e.g. ethylselenenyl group, butylselenenyl group, phenylselenenyl group and the like, substituted phosphino groups represented by the formula, $R^7R^8P$, e.g. diphenylphosphino group, and halogen atoms such as chlorine, bromine, iodine and the like. In the above formulas, $R^7$, $R^8$ and $R^9$ may be the same or different and independently represent a monovalent hydrocarbon group having from 1 to 12 carbon atoms, preferably an alkyl group having from 1 to 6 carbon atoms or a phenyl group.

For the preparation of the 2,5-reactive substituent group-containing silole of the formula (1), there is used a process wherein a bis-ethynylsilane of the following general formula (3) and an alkali metal or an alkali metal complex are reacted with each other, and the resultant reaction mixture is further reacted with halides of the formulas, $R^5X$ and $R^6X$ wherein $R^1$ to $R^4$ have, respectively, the same meanings as defined hereinbefore.

The alkali metals or alkali metal complexes include, for example, Li, Na, K or complexes obtained by adding, to these alkali metals, condensed aromatic compounds such as naphthalene, substituted condensed aromatic compounds such as 4,4'-bis(tert-butyl)-biphenyl, and amines such as 1-dimethylaminonaphthalene, liquid ammonia and the like. Of these, lithium naphthalide is preferred.

The reaction between the silane of the formula (3) and the alkali metal or alkali metal complex is preferably effected at a molar ratio of 1:2 to 10, more preferably 1:2.5 to 4. The use of the alkali metal or alkali metal complex in excess can suppress side reactions. The reaction temperature is preferably in the range of −78° C. to room temperature, more preferably from −40° C. to 0° C. The reaction time is generally in the range of from 0.5 to 8 hours.

For the reaction, it is preferred to use a solvent. Such solvents may be ones which are able to dissolve the silane of the formula (3). For instance, aproic, polar solvents such as tetrahydrofuran (THF), dimethylformamide (DMF) and the like are preferably used. The amount of the solvent is usually in the range of 2 to approximately 100 times the volume of the silane.

The compound of the formula (1) of the invention can be prepared by reacting the halides of the formulas, $R^5X$ and $R^6X$, wherein $R^5$ and $R^6$ have, respectively, the same meanings as defined before and X represents a halogen atom, with the reaction mixture of the silane of the formula (3) and an alkali metal or alkali metal complex. The halides of $R^5$ and $R^6X$ are preferably chlorides or bromides of the formulas wherein X is Cl or Br in view of the reactivity and the ease in handling. If it is intended to obtain compounds of the formula (1) wherein $R^5$ and $R^6$ are, respectively, a halogen atom, a halogen itself may be used as $R^5X$ and $R^6X$. Alternatively, there may be used complexes of amine salts of hydrogen halides and halogens such as pyridinium hydrobromide perbromide. It will be noted that $R^5$ and $R^6X$ may be the same or different. More particularly, where compounds of the formula (1) wherein $R^5$ and $R^6X$ are the same are obtained, $R^5X$ and $R^6X$ should be the same compound, i.e. one halide is used as both as $R^5X$ and $R^6X$.

The total amount of $R^5X$ and $R^6X$ is in the range of from 2 to 10 moles, preferably from 2 to 4 moles, per mole of the silane of the formula (3). The reaction temperature is preferably in the range of from −78° C. to room temperature and the reaction time is generally in the range of from 1 to 8 hours.

The reaction mixture of the silane of the formula (3) and an alkali metal or alkali metal complex is subjected to reaction with $R^6X$ and $R^6X$ as it is. The reaction mixture contains therein a 2,5-reactive substituent group (alkali metal)-containing silole which is an intermediate of the following formula (2). This silole is reacted with $R^5X$ and $R^6X$ to provide an intended substance of the following formula (1). The reaction between the intermediate of the formula (2) and $R^5$ and $R^6X$ proceeds substantially stoichiometrically.

The silole of the formula (1) according to the invention is substituted with a monovalent hydrocarbon-substituted S, Se, Si, Ge, Sn or P, or a halogen atom at the 2,5 positions thereof and is reactive. For instance, a silole of the formula (1) wherein $R^5$ and $R^6$ are, respectively, a bromine atom is subjected to coupling reaction with (phenylethynyl)trimethylstannane in the presence of a palladium catalyst, thereby obtaining a silole which is substituted with the phenylethynyl group at the 2,5 positions. Likewise, the coupling reaction with (2-thienyl)tributylstannane in the presence of a palladium catalyst results in the preparation of a silole which is substituted with the thienyl group at the 2,5 positions. Thus, the silole can be used to form copolymers with other π-conjugated polymers known as a functional material or starting monomers of the polymers. The siloles of the invention exhibit a specific π-electron system and are thus useful as a starting material for preparing photoelectron functional materials. In particular, the siloles are conveniently used as a starting material for preparing optical function materials, such as conductive organic materials, non-linear optical materials and photoresponse materials, which are excellent in processability.

Another class of 2,5-reactive substituent group-containing silole according to the invention is of the following formula (4)

wherein $R^1$ to $R^4$ have, respectively, the same meanings as defined before, provided that preferably in the formula (4), $R^1$ to $R^4$ independently represent a substituted or unsubstituted alkyl having from 1 to 10 carbon atoms, a cycloalkyl group or an aryl group, X represents a halogen atom, and M has the same meaning as defined before provided that in the formula (4), M preferably represents an alkali metal atom.

In the formula (4), it is preferred that $R^1$ and $R^2$, respectively, represent an alkyl group, and $R^3$ and $R^4$, respectively, represent an aryl group. Examples of the alkyl group include methyl, ethyl, n-propyl, isopropyl and the like, examples of the cycloalkyl group include a cyclohexyl group, and examples of the aryl group include phenyl, tolyl, xylyl and the like. The halogen atom includes, for example, chlorine, bromine, iodine or the like. The alkali metal includes, for example, lithium, sodium, potassium or the like.

The silole of the formula (4) can be obtained by reaction between a dihalogenosilole of the following formula (6) and an alkylated product of an alkali metal wherein $R^1$ to $R^4$ and X have, respectively, the same meanings as defined before.

The silole of the formula (6) can be obtained by a process as set out hereinabove. Thus, the silole of the formula (6) corresponds to a compound of the formula (1) wherein $R^5$ and $R^6$ are, respectively, a halogen atom.

The alkylated product of an alkali metal used to reaction with the silole of the formula (6) includes, for example, methyl lithium, n-butyl lithium, tert-butyl lithium or the like. The amount is preferably in the range of 0.5 to 2 moles per mole of the silole.

This reaction can be carried out in a solvent such as diethyl ether at a temperature from −110° C. to 0° C. For instance, the alkylated product of an alkali metal is added at −78° C., followed by gradually increasing the temperature and completing the reaction at approximately 0° C. The reaction time is usually in the range of 5 to 60 minutes.

A silole polycondensate according to a further embodiment of the invention is of the following formula (5)

wherein $R^1$ and $R^4$ have, respectively, the same meanings as defined before, A and B may be the same or different and independently represent a hydrogen, a halogen atom or an alkali metal atom, and n is an integer of 2 or over. The silole polycondensate of the formula (5) can be obtained by subjecting the silole or silole polycondensate of the following formula (7) to polycondensation (oxidative coupling reaction) under oxidative conditions in the presence of a cuprous compound wherein $R^1$ to $R^4$, M and X have, respectively, the same meanings as defined before, m is an integer of 1 or over provided that n>m.

More specifically, when the silole or silole polycondensate of the formula (7) is polycondensed under oxidative conditions in the presence of a cuprous compound, there can be obtained a silole polycondensate of the formula (5a) wherein X is a halogen atom.

The silole polycondensate is obtained when the compound of the formula (7) is subjected to the oxidative coupling reaction as depicted above. Examples of the cuprous compound used for the oxidative coupling reaction include copper bromide (CuBr), copper iodide (CuI), cuprous cyanide (CuCN) and the like. The amount should preferably in the range of 0.5 to 2 moles per mole of the compound of the formula (7). The oxidative coupling reaction may be carried out using 0.5 to 10 moles of oxidizing agents, such as p-dinitrobenzene, o-dinitrobenzene, tetracyanoquinodimethane (TCNQ), $CuCl_2$ and the like, per mole of the compound of the formula (7). Alternatively, air or oxygen may be bubbled for the oxidative couping reaction.

The solvent for the reaction includes, for example, tetrahydrofuran, 2-methylhydrofuran, diethylene glycol dimethyl ether, hexamethylphosphoramide or the like. The reaction system should preferably in an atmosphere of an inert gas such as dried nitrogen, argon or the like and the reaction temperature is in the range of −130° to 0° C. The reaction time is usually in the range of 30 minutes to 3 hours.

The silole polycondensate of the formula (5a) obtained according to the above process can be obtained by reaction with an alkylated product of an alkali metal in the same manner as in the process for preparing the silole of the afore-indicated formula (4) whereby a compound of the formula (5a) wherein one of X's is replaced by an alkali metal M (i.e. a silole condensate of the formula (7) wherein m≧2, or a silole condensate of the formula (5) wherein A is a halogen atom and B is an alkali metal). This silole polycondensate may be used as a starting material for preparing a silole polycondensate of the formula (5).

A polycondensate of the formula (5) wherein both A and B are an alkali metal can be obtained by reaction of the alkylated product of an alkali metal in an amount of two times by mole larger than in the above case. Moreover, a polycondensate of the formula (5) wherein both or either of A and B is a hydrogen atom can be obtained by acting water on the alkali metal adduct.

The polycondensate (9) in the formula (5) wherein both A and B are a hydrogen atom can be obtained by reaction between a dialkali silole of the following formula (8) and a reactive halogen-containing compound, followed by condensation in the presence of an iron (III) acetylacetonate catalyst.

wherein $R^1$ to $R^4$ and M have, respectively, the same meanings as defined before, and p is an integer of 2 or over.

The silole of the formula (8) corresponds to that of the formula (2) and can be obtained as set out above. The reactive halogen-containing compound reacts with the excess alkali metal or alkali metal complex to remove them. Any compound capable of removing the alkali metal or alkali metal complex may be used including triarylhalosilanes such as triphenyl-silyl chloride. The amount is preferably in the range of 2 to 3 moles per mole of the silole of the formula (8). The amount of the iron (III) acetylacetonate is in the range of from 0.5 to 2 moles per mole of the silole of the formula (8).

The reaction between the reactive halogen-containing compound and the reaction mixture containing the silole of the formula (8) should preferably be effected in a solvent such as tetrahydrofuran and the reaction temperature is preferably in the range of from 0° to 60° C. The reaction time is usually in the range of 10 to 60 minutes. The reaction with the iron (III) acetylacetonate may be likewise carried out in a solvent. The reaction time is preferably in the range of from 0° to 60° C. and the reaction time usually ranges from 30 minutes to 24 hours.

The present invention further provides 2,5-different reactive substituent groups-containing siloles of the following formula (10). This silole can be obtained by reaction between the silole of the formula (4) and a compound represented by AX wherein $R^1$ to $R^4$ and X have, respectively, the same meanings as defined before, and A represents a monovalent hydrocarbon group-substituted sulfur, selenium, silicon, germanium, tin or phosphorus. The groups represented by A include a substituted silyl group, a substituted germyl group, a substituted stannyl group, a substituted selenyl group, and a substituted phosphino group. More specifically, the substituted silyl group is represented by the formula, $R^7R^8R^9Si$, e.g. trimethylsilyl group, tributylsilyl group, phenyldimethylsilyl group and the like, the substituted germyl group is represented by the formula, $R^7R^8R^9Ge$, e.g. trimethylgermyl group, the substituted stannyl group is represented by the formula, $R^7R^8R^9Sn$, e.g. trimethylstannyl group, tributylstannyl group, phenyldimethylstannyl group and the like, the substituted selenyl group is represented by the formula, $R^7Se$, e.g. ethylselenenyl group, butylselenenyl group, phenylselenenyl group and the like, and the substituted phosphino group is represented by the formula, $R^7R^8P$, e.g. diphenylphosphino group.

Where a compound of AX is reacted with the silole of the formula (4), the compound, AX, is used in an amount of from 1 to 3 moles per mole of the silole of the formula (4). The reaction temperature is preferably from 0° to 60° C. and the reaction time is usually from 10 to 60 minutes.

The silole of the formula (10) is used for polycondensation in the presence of a palladium catalyst to provide a silole polycondensate.

The siloles or silole polycondensates of the invention are able to form copolymers with other types of π-conjugated polymers known as a functional material or monomers thereof. The silole polycondensates of the invention exhibit a specific π-electron characteristic and are useful as a starting material for preparing photoelectron functional materials. In particular, they are favorable as a starting material for preparing optical functional materials such as conductive organic materials, non-linear optical materials and photoresponse materials.

The invention is more particularly described by way of examples, which should not be construed as limiting the invention. In the examples, Me represents a methyl group, Et represents an ethyl group, Ph represents a phenyl group, $^iPr$ represents an isopropyl group, and Hex represents a hexyl group.

EXAMPLE 1

A mixture of 256 mg (2 mmols) of naphthalene and 14 mg (2 mmols) of lithium was agitated in 5 ml of dried THF at room temperature in a stream of argon for 3 hours, thereby providing 270 mg of lithium naphthanide. Dimethyldi(phenylethynyl)silane, 130 mg (0.5 mmols), was added dropwise to THF solution of the resultant lithium naphthanide at room temperature, followed by mixing for 15 minutes to obtain the THF solution of 4.8 g of a mixture (I) of 2,5-dilithio-1, 1-dimethyl-3,4-diphenylsilole and lithium naphthalenide.

Then, 217 mg (2 mmols) of trimethylsilyl chloride was added to 4.8 g of the mixture (I) (corresponding to 0.5 mmols of 2,5-dilithio-1,1-dimethyl-3,4-diphenylsilole), followed by agitation at room temperature for 1 hour and concentration under reduced pressure. The resultant reaction mixture was purified according to liquid chromatography to obtain 175 mg of 2,5-bis (trimethylsilyl)-1,1-dimethyl-3,4-diphenylsilole (yield: 86%).

Properties: white crystals with a melting point of 100° C.

Values of elementary analysis for $C_{24}H_{34}Si_3$ Calcd.: C; 70.86%, H; 8.24% Found: C; 70.93%, H; 8.61%

$^1$HNMR: δ −0.16 (s, 18H) 0.40 (s, 6H) 6.8 to 6.87 (m, 4H) 6.98 to 7.07 (m, 6H)

$^{13}$CNMR: δ −2.86 0.66 125.96 126.90 128.69 142.84 144.73 168.63

EXAMPLE 2

The general procedure of Example 1 was repeated except that 159 mg of diisopropyldi-(phenylethynyl)silane was used instead of the dimethyl (phenylethynyl) silane, thereby obtaining 4.86 g of a mixture (II) of 2,5-dilithio-1,1-diisopropyl-3,4-diphenylsilole and lithium naphthalenide.

In the same manner as in Example 1, the mixture (II) was used to obtain 2,5-bis-(trimethylsilyl)-1,1-diisopropyl-3,4-diphenylsilole having the following properties and analytical values in a yield of 73%.

Properties: white crystals with a melting point of 107° C.

Values of elementary analysis for $C_{28}H_{42}Si_3$ Theoretical: C; 72.65%, H; 9.14% Found: C; 72.68%, H; 9.28%

$^1$HNMR: δ −0.16 (s, 18H) 1.16 (d, J =4.7 Hz, 12H) 1.46 (sep, J =7.4 Hz) 6.75 to 6.84 (m, 4H) 6.96 to 7.06 ( m, 6H)

$^{13}$CNMR δ 1.11 11.80 18.34 126.03 126.85 129.10 140.75 143.37 171.86

EXAMPLE 3

The general procedure of Example 1 was repeated except that 200 mg of dihexyldi(phenylethynyl)silane was used instead of the dimethyl (phenylethynyl) silane, thereby obtaining 4.90 g of a mixture (III) of 2,5-dilithio-1,1-dihexyl-3,4-diphenylsilole and lithium naphthalenide.

In the same manner as in Example 1, the mixture (III) was used to obtain 2,5-bis-(trimethylsilyl)- 1,1 -dihexyl -3,4 -diphenylsilole having the following properties and analytical values at a yield of 86%.

Properties: white crystals with a melting point of 81° C.

Values of elementary analysis for $C_{34}H_{54}Si_3$ Calcd.: C; 74.65%, H; 9.95% Found: C; 74.60%, H; 9.88%

$^1$HNMR: δ −0.16 (s, 18H) 0.86 to 1.02 (m, 10H) 1.24 to 1.44 (m, 16H) 6.78 to 6.85 (m, 4H) 6.97 to 7.07 (m, 6H)

$^{13}$CNMR δ 0.66 3.64 2.70 3.91 31.68 33.18 125.93 126.85 128.80 142.77 143.08 170.55

EXAMPLE 4

The general procedure of Example 3 was repeated except that 0.54 ml ( 2 mmols ) of tributylstannyl chloride was used instead of the trimethylsilyl chloride for reaction with the mixture (III ), thereby obtaining 2,5-bis-(tributylstannyl)-1,1-dihexyl-3,4-diphenylsilole having the following properties and analytical values at a yield of 49%.

Properties: colorless, viscous oil

Values of elementary analysis for $C_{52}H_{90}SiSn_2$ Calcd.: C; 63.68%, H;9.25% Found: C;63.48%, H;9.40%

$^1$HNMR: δ 0.51 to 0.66 (m, 12H) 0.76 to 0.94 (m, 28H) 1.10 to 1.46 (m, 40H) 6.84 to 6.91 (m, 4H) 6.98 to 7.06 (m, 6H)

$^{13}$CNMR 10.49 13.23 13.60 14.16 22.68 24.25 27.48 29.25 31.78 33.41 125.95 127.06 128.43 145.14 147.91 169.80

EXAMPLE 5

The general procedure of Example 1 was repeated except that 401 mg (2.1 mmols) of phenylselenenyl chloride was used instead of the trimethylsilyl chloride for reaction with the mixture (I), thereby obtaining 1,1-dimethyl-3,4-diphenyl-2,5-di(phenylselenenyl)silole having the following properties and analytical values at a yield of 74%.

Properties: yellow crystals with a melting point of 121° C.

Values of elementary analysis for $C_{30}H_{26}SiSe_2$ Calcd.: C;62.94%, H;4.58% Found: C;63.15%, H;4.67%

$^1$HNMR: δ −0.33 (s, 6H) 6.99 to 7.06 (m, 4H) 7.12 to 7.28 (m, 12H) 7.58 to 7.66 (m, 4H)

$^{13}$CNMR δ −2.87 126.94 127.60 128.13 128.71 129.02 135.22 136.19 139.16 153.65

UV-Vis: 247 nm (Log ϵ=4.26) 296 nm (Log ϵ=3.96) 386 nm (Log ϵ=3.92)

EXAMPLE 6

The general procedure of Example 1 was repeated except that a THF solution of triphenylsilyl chloride (295 mg, 1 mmol) was used instead of the trimethylsilyl chloride and was added to the mixture (I), 20 minutes after which a THF solution of pyridinium hydrobromide perbromide (320 mg, 1 mmol), thereby obtaining 2,5-dibromo-1,1-diisopropyl-3,4-diphenylsilole having the following properties and analytical values in a yield of 44%.

Properties: white crystals with a melting point of 126° C.

Values of elementary analysis for $C_{22}H_{24}SiBr_2$ Calcd.: C; 55.48%, H; 5.08% Found: C; 55.52%, H; 5.02%

$^1$HNMR: δ 1.25 (d, J=7.0 Hz, 12H) 1.47 (sep, J=7.0 Hz, 2H) 6.88 to 6.98 (m, 4H) 7.10 to 7.20 (m, 6H)

$^{13}$CNMR δ 9.82 17.17 119.79 127.32 127.53 128.95 137.30 157.89

EXAMPLE 7

The general procedure of Example 6 was repeated except that the mixture (III) of Example 3 was used instead of the mixture (I) and bromine was used instead of the THF solution of pyridinium hydrobromide perbromide, thereby obtaining 2,5-dibromo-1,1-dihexyl-3,4-diphenylsilole having the following properties and analytical values in a yield of 46%.

Properties: white crystals with a melting point of 64° C.

Values of elementary analysis for $C_{28}H_{36}SiBr_2$ Calcd.: C; 60.00%, H; 6.47% Found: C; 60.08%, H; 6.57%

$^1$HNMR: δ 0.85 to 1.10 (m, 10H) 1.2 to 1.7 (m, 16H) 6.9 to 7.0 (m, 4H) 7.10 to 7.2 (m, 6H)

$^{13}$CNMR δ 9.73 14.14 22.58 22.88 31.43 32.69 121.86 127.35 127.52 128.96 137.21 156.84

EXAMPLE 8

The general procedure of Example 1 was repeated except that 192 mg of diphenyldi(phenylethynyl)silane was used instead of the dimethyl(phenylethynyl)silane to obtain 4.89 of a mixture (IV) of 2,5-dilithio-1,1-diphenyl- 3,4 -diphenylsilole and lithium naphthalenide.

EXAMPLE 9

Dried diethyl ether ( 10 ml ) was added to 7 mg ( 0.95 mmols) o f 2,5-dibromo-1,1-diethyl- 3,4-diphenylsilole, followed by cooling down to −78° C. and dropwise addition of 0.7 ml of 1.64 M of n-butyl lithium. The reaction mixture was allowed to warm gradually to 0° C. and subjected to reaction at 0° C. for 3 hours to obtain a compound of the following formula (V)

The resultant reaction mixture was subjected to the following reaction and the resultant product was confirmed to have the same formula.

(1) Preparation of 2-bromo-1,1-diethyl-3,4-diphenylsilole

Water (100 µl) was added to the reaction mixture of the formula (V) for deactivation, to which about 1 g of anhydrous sodium sulfate was added for drying, followed by filtration using a filter paper. The resultant filtrate was subjected to distillation under reduced pressure to remove the solvent therefrom. The resulting residue was subjected to silica gel column chromatography ( hexane, Rf=0.35) to obtain 2.89 mg of a colorless liquid consisting of 2-bromo-1,1-diethyl-3,4-diphenylsilole of the 5 following formula (VII) in a yield of 82%.

(VII)

The physical properties are shown below.
$^1$HNMR: δ 0.83 to 0.98 (m, 4H) 1.02 to 1.12 (m, 6H) 6.09 (s, 1H) 6.92 to 7.14 (m, 7H) 7.1 to 7.22 (m, 3H)

EXAMPLE 10

Preparation of 2-bromo-1,1-diethyl-3,4-diphenyl-5-trimethylsilylsilole

The general procedure of Example 9 was repeated except that 450 mg (1 mmols) of 2,5-dibromo-1,1-diethyl-3,4-diphenylsilole was used. Thereafter, 0.19 ml ( 1.5 mmols) of trimethylchlorosilane was added for the deactivation in place of water used in Example 9 (1), followed by the same procedure of Example 9 to obtain 351 mg of a colorless liquid 2-bromo-1,1-diethyl-3,4-diphenyl-5-trimethylsilylsilole of the following formula (VIII) in a yield of 79%.

(VIII)

The physical properties are shown below.
$^1$HNMR δ –0.16 (s, 9H) 0.86 to 1.18 (m, 10H) 6.83 to 6.93 (m, 4H) 7.02 to 7.14 (m, 6H) Rf: 0.23 (hexane)

EXAMPLE 11

Preparation of 2-bromo-1,1-diethyl -3,4-diphenyl-5-tributylstannysilole

The general procedure of Example 10 was repeated using 0.42 ml (1.50 mmols) of tri(n-butyl)chlorostannane instead of trimethyl-chlorosilane, thereby obtain 640 mg of a colorless liquid compound o f the following formula (IX) in a yield of 84%.

(IX)

The physical properties are shown below.
$^1$HNMR δ 0.53 to 0.63 (m, 6H) 0.78 to 0.97 (m, 119H) 1.10 to 1.50 (m, 28H) 6.80 to 6.88 (m, 2H) 6.88 to 6.96 (m, 2H) 7.02 to 7.16 (m, 6H) Rf: 0.50 (hexane)

EXAMPLE 12

Preparation of 5,5'-dibromo-1,1,1'-tetraethyl-3,3,3',3'-tetraphenyl-2,2'-bisilole A suspension of 186 mg (0.415 mmols) of 2,5-dibromo-1,1-diethyl-3,4-diphenylsilole in 1 ml of diethyl ether was cooled down to –78° C., followed by addition of 290 µl of n-butyllithium (1.59 M hexane solution) (0.437 mmols). The reaction container was gradually heated and the reaction was effected at –10° C. for 3 hours. After completion of the reaction, the side product butyl bromide and the diethyl ether were removed under a reduced pressure at a temperature of 0 to 10° C., followed by substitution of the atmosphere with an argon. While introducing argon, 18 mg (0.2 mmols) of copper cyanide (CuCN) was added in the form of a solid and mixed. The reaction system was again cooled to –78° C., to which 1 ml of tetrahydrofuran was added, followed by heating the mixture under agitation for reaction at 0° C. for 2 minutes, resulting in conversion into a dark green solution. Immediately, the solution was cooled back to –78° C. and maintained for 13 minutes. Thereafter, 90 µl (0.6 mmols) of tetramethylethylenediamine was added, following by keeping for 35 minutes. Subsequently, a solution of 336 mg (2 mmols) of p-dinitro-benzene in 2 ml of tetrahydrofuran was added to the solution for oxidation. The reaction solution was changed into a yellowish brown suspension. The reaction was conducted at –78° C. for 1 hour. Then, 2 ml of a mixed solution of (a saturated aqueous solution of sodium hydrogen sulfite)/methanol in equal amounts was added for reduction. The reaction solution was turned into a yellow suspension. To the suspension was added 20 ml of a 1N hydrochloric acid aqueous solution at room temperature to make it acidic, followed by extraction with diethyl ether and washing the resultant organic phase with a calcium chloride saturated solution. The organic phase was dried with anhydrous sodium sulfate and filtered, after which the solvent was distilled off under reduced pressure. The resultant residue was subjected to Florisil column chromatography (hexane, Rf=0.22) to obtain 106 mg of a compound having the following structural formula (X) in the form of yellow crystals in a yield of 69%.

(X)

The physical properties are shown below.
Melting point: 157 to 159° C. (decomposition)
$^1$HNMR δ 0.14 (m, 4H) 0.41 (m, 4H) 0.77 (t, J=7.8 Hz, 12H) 6.87 to 6.95 (m, 4H) 6.96 to 7.06 (m, 4H) 7.07 to 7.18 (m, 12H)

$^{13}$CNMR δ 2.43 7.47 124.71 126.81 127.35 127.85 129.04 130.81 137.97 139.46 141.40 156.39 157.89

Elementally analysis calculated for $C_{40}H_{40}Si_2Br_2$ C; 65.21%, H; 5.47% Found:C; 65.43%, H; 5.52%

EXAMPLE 13

5,5'-Dibromo-1,1,1',1'-tetraethyl-3,3,3', 3'-tetraphenyl-2,2'-bisilole, 113 mg (0.154 mmols), prepared in Example 12 was dissolved in 4 ml of diethyl ether to provided a yellow solution, to which a pentane solution of t-BuLi (1.61M, 210 μl, 0.34 mmols) was added at −78° C. Immediately, the solution was changed into a dark red color, followed by agitation under similar temperature conditions for 1 hour. An ice bath was used to increase the temperature up to 0° C. and the solvent was removed under reduced pressure at 0° C. for 10 minutes. The flask was purged with argon and 6.9 mg (0.0077 mmols) of copper cyanide was added to a solid reaction mixture in a stream of argon. The reaction mixture was cooled down to −78° C., into which 3 ml of dried THF was introduced. The resultant dark red suspension was heated to −40° C. and agitated, whereupon the reaction mixture changed into a dark red solution. At −40° C., 70 μl (0.46 mmols) of TMEDA was added to the reaction mixture. The mixture was agitated for 1 hour in the range of −40° C. to −20° C., followed by cooling down to −78° C. A THF solution (3 ml) of 134 mg (0.8 mmols) of p-nitrobenzene was added to the solution through a transfer tube. The resultant yellowish brown suspension was agitated under similar temperature conditions for 1 hour, into which 2 ml of a saturated mixed solution of $NaHSO_3$ and MeOH at a ratio of 1:1 was introduced under conditions of −78° C. by use of a syringe. The resultant yellowish orange suspension was returned to room temperature, followed by dilution with a 1NHCl solution. $Et_2O$ was used for extraction and the resultant organic phase was washed with a saline solution, followed by drying over anhydrous $Na_2SO_4$ and concentration under reduced pressure. 1,2-Dichloroethane (5 ml) was added to the resultant concentrate, whereupon an orange-colored precipitate was obtained. After filtration and washing with $Et_2O$, the precipitate was dissolved in about 3 ml of a mixed solution hexane and $CH_2C_2$ (1:1), followed by column chromatography using Florisil to obtain 16.7 mg of a compound of the following formula (XI) (yield: 16%) in the form of an orange solid. Rf=0.58 (hexane/$CH_2C_2$=2/1).

Melting point: 287° to 289° C. (decomposition)

$^1$HNMR δ −1.20 to −0.34 (br m, 8H) −0.05 to 0.25 (br m, 2H) 0.25 to 0.70 (m, 24H) 0.82 to 1.10 (m, 6H) 6.60 to 7.55 (br m, 40H)

UV-vis ($CHCl_3$) $v_{max}$ nm (log ε) 243 (4.75) 282 (4.62) 378 (sh, 3.97) 443 (4.21)

FABMS 1310 (M$^+$) 1312, 1314

Anal. Calcd. for $C_{80}H_{80}Br_2Si_4$: C, 73.14; H, 6.14 Found: C, 72.89; H, 6.16

EXAMPLE 14

Preparation of H

A solution of triphenylsilyl chloride (590 mg, 2 mmols) in dried THF (4 ml) was added to a THF solution of 1,1-diisopropyl-2,5-dilithiosilole (1 mmol) and agitated for 30 minutes. A THF (6 ml) solution of iron (III) acetylacetanate (494 mg, 1.4 mmols) was added to the reaction mixture at room temperature. The resultant yellowish orange suspension was agitated at room temperature for 12 hours and filtered. The resultant filtrate was concentrated under reduced pressure. The resulting residue was subjected to silica gel column chromatography (Rf of hexane=0.13) to obtain 77 mg of a crude product in the form of a yellow solid. This product was recrystallized from a mixed solvent of hexane and ethyl ether to obtain 30 mg of yellow crystals of 1,1,1',1'-tetraisopropyl-3,3'-4,4'-tetraphenyl-2,2'-bisilole in a yield of 9%.

Figure 1:
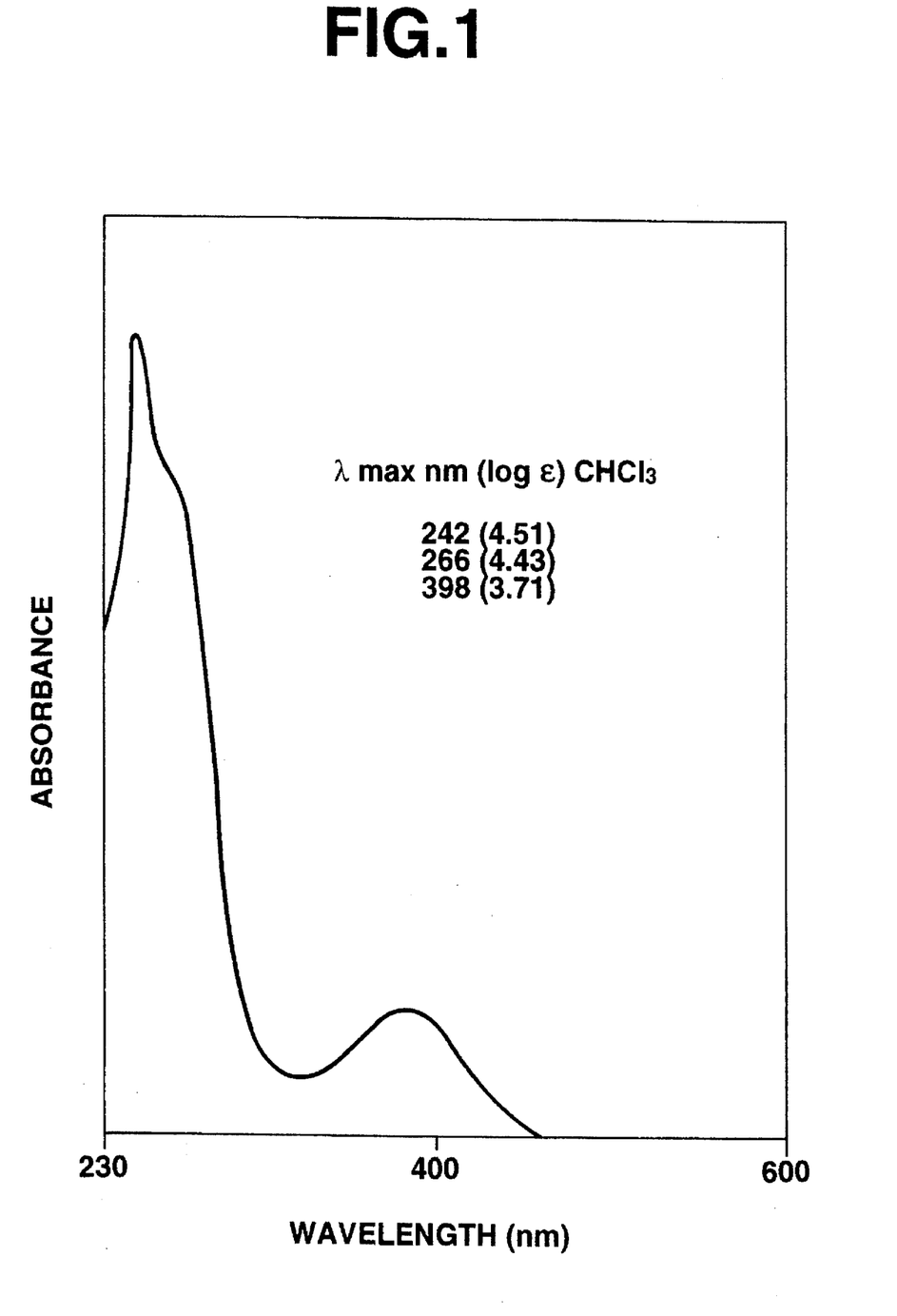
FIG. 1 is a UV absorption spectrum chart of a compound of Example 14.

The physical properties are shown below. In FIG. 1, there is shown a UV absorption spectral chart of the compound.

Melting point: 202° C.

$^1$HNMR δ 0.2 to 0.4 (m, 2H) 0.84 (d, J=7.4 Hz, 6H) 0.90 (d, J=7.4 Hz, 6H) 5.95 (s, 2H) 6.87 to 6.96 (m, 4H) 7.02 to 7.14 (m, 6H)

$^{13}$CNMR δ 11.49 19.16 20.03 126.17 126.51 127.21 127.36 127.82 128.39 130.74 140.24 142.30 145.58 153.11 162.96

UV-vis: 242 nm (log ε=4.51), 266 nm (sh., log ε=4.43), 398 nm (log ε=3.71)

MS: m/e 634 (M$^+$, 100), 591 (41)

Elementary analysis: calculated for $C_{44}H_{50}Si_2$:C;83.22%, H;7.94% found: C;82.95%, H;8.01%

What is claimed is:

1. A 2,5-reactive substituent group-containing silole of the following general formula (1)

wherein $R^1$ to $R^4$ may be the same or different and independently represent a monovalent hydrocarbon group having from 1 to 12 carbon atoms or a hydrogen atom, and $R^5$ and $R^6$ may be the same or different and independently represent a group selected from monovalent hydrocarbon-substituted sulfur, selenium, silicon, germanium tin and phosphorus, or a halogen atom.

2. A 2,5-reactive substituent group-containing silole of the following general formula (2)

(2)

wherein $R^1$ to $R^4$ may be the same or different and independently represent a monovalent hydrocarbon group having from 1 to 12 carbon atoms or a hydrogen atom, and M represents an alkali metal.

3. A process for preparing a 2,5-reactive substituent group-containing silole defined in claim 2, comprising the step of reacting a silane compound of the following formula (3)

(3)

wherein $R^1$ to $R^4$ may be the same or different and independently represent a monovalent hydrocarbon group having from 1 to 12 carbon atoms or a hydrogen atom, with an alkali metal or an alkali metal complex.

4. A 2,5-reactive substituent group-containing silole of the following formula (4)

(4)

wherein $R^1$ to $R^4$ may be the same or different and independently represent a substituted or unsubstituted alkyl group having from 1 to 10 carbon atoms, a cycloalkyl group or an aryl group, X represents a halogen atom and M represents an alkali metal.

5. A silole polycondensate of the following formula (5)

(5)

wherein $R^1$ to $R^4$ may be the same or different and independently represent a substituted or unsubstituted alkyl group having from 1 to 10 carbon atoms, a cycloalkyl group or an aryl group, A and B may be the same or different and represents a hydrogen atom, a halogen atom or an alkali metal, an n is an integer of 2 or over.

6. A process for preparing a 2,5-reactive substituent group-containing silole defined in claim 8, comprising the step of reacting an alkylated product of an alkali metal with a dihalogenosilole of the following formula (6)

(6)

wherein $R^1$ to $R^4$ may be the same or different and independently represent a substituted or unsubstituted alkyl group having from 1 to 10 carbon atoms, a cycloalkyl group or an aryl group, and X represents a halogen atom.

7. A process for preparing a silole polycondensate defined in claim 5, comprising the step of subjecting a silole or silole polycondensate of the following formula (7)

(7)

wherein $R^1$ to $R^4$ may be the same or different and independently represent a substituted or unsubstituted alkyl group having from 1 to 10 carbon atoms, a cycloalkyl group or an aryl group, X represents a halogen atom and M represents an alkali metal, m is an integer of 1 or more provided that n>m, to polycondensation under oxidative conditions in the presence of a cuprous compound.

8. A process for preparing a silole polycondensate of the following formula (9)

(9)

wherein $R^1$ to $R^4$ may be the same or different and independently represent a substituted or unsubstituted alkyl group having from 1 to 10 carbon atoms, a cycloalkyl group or an aryl group, and p is an integer of 2 or more, comprising the step of reacting a reactive halogen-containing compound with a dialkali silole of the following formula (8)

(8)

wherein $R^1$ and $R^4$ are defined above, and then subjecting the resultant product to polycondensation in the presence of iron (III) acetylacetonate.

9. A 2,5-different reactive substituent groups-containing silole of the following formula (10)

(10)

wherein $R^1$ to $R^4$ may be the same or different and independently represent a substituted or unsubstituted alkyl group having from 1 to 10 carbon atoms, a cycloalkyl group or an aryl group, X represents a halogen atom, and A represents a monovalent hydrocarbon group-substituted sulfur, selenium, silicon, germanium, tin or phosphorus.

10. A process for preparing a 2,5-reactive substituent group-containing silole of the following formula (1)

(1)

wherein $R^1$ to $R^4$ may be the same or different and independently represent a monovalent hydrocarbon group having from 1 to 12 carbon atoms or a hydrogen atom, and $R^5$ and $R^6$ may be the same or different and independently represent a group selected from monovalent hydrocarbon-substituted sulfur, selenium, silicon, germanium, tin and phosphorus, or a halogen atom, comprising the step of reacting a 2,5-reactive substituent group-containing silole of the following formula (2)

(2)

wherein $R^1$ to $R^4$ are defined above and M represents an alkali metal, with halides of the formula $R^5X$ and $R^6X$, wherein $R^5$ and $R^6$ are defined above and X represents a halogen atom.

11. A process for preparing a 2,5-reactive substituent group-containing silole of the following formula (1)

(1)

wherein $R^1$ to $R^4$ may be the same or different and independently represent a monovalent hydrocarbon group having from 1 to 12 carbon atoms or a hydrogen atom, and $R^5$ and $R^6$ may be the same or different and independently represent a group selected from monovalent hydrocarbon-substituted sulfur, selenium, silicon, germanium, tin and phosphorus, or a halogen atom, comprising the steps of reacting a silane compound of the following formula (3)

(3)

wherein $R^1$ to $R^4$ are defined above, with an alkali metal or an alkali metal complex to obtain a reaction mixture, and reacting said reaction mixture with halides of the formulas $R^5X$ and $R^6X$, wherein $R^5$ and $R^6$ are defined above and X represents a halogen atom.

12. A process for preparing a 2,5-different reactive substituent groups-containing silole defined in claim 9, comprising the step of reacting a silole of the following formula (4)

(4)

wherein $R^1$ to $R^4$ may be the same or different and independently represent a substituted or unsubstituted alkyl group having from 1 to 10 carbon atoms, a cycloalkyl group or an aryl group, X represents a halogen atom and M represents an alkali metal, with a compound of the formula, AX, wherein A represents a monovalent hydrocarbon-substituted sulfur, selenium, silicon, germanium, tin or phosphorus and X represents a halogen atom.

13. The 2,5-reactive substituent group-containing silole according to claim 1, wherein $R^1$ to $R^4$ independently represent an alkyl group having from 1 to 10 carbon atoms, an aryl group having from 6 to 10 carbon atoms, or an aralkyl group having from 7 to 12 carbon atoms.

14. The 2,5-reactive substituent group-containing silole according to claim 1, wherein $R^3$ and $R^4$ represent an aryl group having from 6 to 10 carbon atoms.

15. The process for preparing a 2,5-reactive substituent group-containing silole of formula (1) according to claim 11, wherein the molar ratio of the silane compound of formula (3) to the alkali metal or alkali metal complex is 1:2 to 10.

16. The process for preparing a 2,5-reactive substituent group-containing silole of formula (1) according to claim 11, wherein the silane compound of formula (3) is reacted with the alkali metal or alkali metal complex at a temperature from −78° C. to room temperature for 0.5 to 8 hours.

17. The process for preparing a 2,5-reactive substituent group-containing silole of formula (1) according to claim 11, wherein 2 to 10 moles of the halides are reacted per mole of the silane compound of formula (3).

18. The 2,5-reactive substituent group-containing silole of formula (4) according to claim 4, wherein $R^1$ and $R^2$ represent an alkyl group, $R^3$ and $R^4$ represent an aryl group, X represents chlorine, bromine or iodine, and M represents lithium, sodium or potassium.

19. The process for preparing a 2,5-reactive substituent group-containing silole of formula (4) according to claim 6, wherein the alkylated product is selected from the group consisting of methyl lithium, n-butyl lithium and tert-butyl lithium.

20. The process for preparing a 2,5-reactive substituent group-containing silole of formula (4) according to claim 6, wherein 0.5 to 2 moles alkylated product is reacted per mole of the silole of formula (6).

21. The process for preparing a 2,5-reactive substituent group containing silole of formula (4) according to claim 6, wherein the alkylated product is reacted with the silole of formula (6) at a temperature from −110° C. to 0° C. for 5 to 60 minutes.

22. The process for preparing a silole polycondensate of formula (5) according to claim 7, wherein the cuprous compound is selected from the group consisting of copper bromide, copper iodide and cuprous cyanide.

23. The process for preparing a silole polycondensate of formula (5) according to claim 7, wherein 0.5 to 2 moles cuprous compound is reacted per mole of the compound of formula (7).

24. The process for preparing a silole polycondensate of formula (9) according to claim 8, wherein 2 to 3 moles reactive halogen-containing compound and 0.5 to 2 moles iron (III) acetylacetonate are reacted per mole of the silole of formula (8).

25. The process for preparing a silole polycondensate of formula (9) according to claim 8, wherein the reactive halogen-containing compound is reacted with the silole of formula (8) at a temperature from 0° to 60° C. for 10 to 60 minutes and the iron (III) acetylacetonate is reacted with the resultant product of the reaction between the reactive halogen-containing compound and the silole of formula (8) at a temperature of 0° to 60° C. for 30 minutes to 24 hours.

26. The silole polycondensate according to claim 5, wherein A and B each represent a hydrogen atom.

27. The 2,5-different reactive substituent groups-containing silole according to claim 9, wherein A represents a substituted silyl group, a substituted germyl group, a substituted stannyl group, a substituted selenenyl group and a substituted phosphino group.

28. The 2,5-different reactive substituent groups-containing silole according to claim 9, wherein A is selected from the group consisting of trimethylsilyl, tributylsilyl, phenyldimethylsilyl, trimethylgermyl, trimethylstannyl, tributylstannyl, phenyldimethylstannyl, ethylselenenyl, butylselenenyl, phenylselenenyl and diphenylphosphino.

29. The process for preparing a 2,5-different reactive substituent groups-containing silole according to claim 9, wherein 1 to 3 moles of the compound of AX is reacted per mole of the silole of formula (4).

30. The process for preparing a 2,5-different reactive substituent groups-containing silole according to claim 9, wherein the silole of formula (4) is reacted with a compound of the formula AX at a temperature of 0° to 60° C. for 10 to 60 minutes.

31. The 2,5-reactive substituent group-containing silole according to claim 1, wherein $R^5$ and $R^6$ is selected from the group consisting of trimethylsilyl, tributylsilyl, phenyldimethylsilyl, trimethylgermyl, trimethylstannyl, tributylstannyl, phenyldimethylstannyl, ethylselenenyl, butylselenenyl, phenylselenenyl and diphenylphosphino.

* * * * *